United States Patent [19]

Onishi

[11] Patent Number: 5,214,067

[45] Date of Patent: May 25, 1993

[54] FUNGICIDAL COMPOSITIONS AND METHOD

[75] Inventor: Janet C. Onishi, Mountainside, N.J.

[73] Assignee: Merck & Co., Inc., Rahway, N.J.

[21] Appl. No.: 583,112

[22] Filed: Sep. 17, 1990

[51] Int. Cl.$^5$ .............................................. A61K 31/335
[52] U.S. Cl. ..................................... 514/449; 514/459
[58] Field of Search .................................. 514/449, 459

[56] References Cited

U.S. PATENT DOCUMENTS

| | | | |
|---|---|---|---|
| 4,389,410 | 6/1983 | O'Hanlon et al. | 424/283 |
| 4,751,237 | 6/1988 | Chabala et al. | 514/449 |
| 4,952,604 | 5/1989 | Hensens et al. | 514/459 |
| 4,988,697 | 1/1991 | Onishi | 514/252 |

FOREIGN PATENT DOCUMENTS

| | | |
|---|---|---|
| 003069 | 7/1979 | European Pat. Off. |
| 0234752 | 9/1987 | European Pat. Off. |

*Primary Examiner*—Frederick E. Waddell
*Assistant Examiner*—Russell Travers
*Attorney, Agent, or Firm*—Salvatore C. Mitri; Charles M. Caruso

[57] ABSTRACT

Novel fungicidal compositions comprising a pyranyl glycine ester compound and a β-lactone compound and a method for controlling mycotic infections is disclosed.

3 Claims, No Drawings

FUNGICIDAL COMPOSITIONS AND METHOD

BACKGROUND OF THE INVENTION

Fungal diseases or mycoses may be superficial, affecting primarily skin, hair and mucous membrane, or may be deep or systemic, affecting lungs and other internal organs. The superficial mycotic infections which are caused by organisms referred to as dermatophytes are generally considered more annoying than serious. The deep or systemic mycotic infections which are caused generally by a different organisms are quite serious, frequently resulting in death.

Antifungal agents considered with specific reference to deep or systemic fungal infections caused by organisms such as Candida species, *Cryptococcus neoformans, Histoplasma capsulatum* and the like, are found for the most part to be fungistatic, i.e., merely inhibit the growth of the fungal organism without effecting a kill. A few fungicidal agents are known. Amphotericin B and other polyenes are known to damage membranes that contain ergosterol and therefore are effectively fungicidal. However, their use is normally precluded because of a number of severe side effects. Other possibly fungicidal drugs have side effects or may be limited by the scope of their spectrum, e.g. 5-fluorocytosine. 5-Fluorocytosine is further limited by the ease with which an organism develops resistance to it. In the search for antifungal drugs, for treating systemic infections, it is desirable to find a drug or a combination of drugs which is effective at low concentration levels thereby minimizing side effects. It is particularly desirable to find a drug or a combination of drugs in which the resultant drug is fungicidal.

STATEMENT OF THE INVENTION

The present invention concerns an improved method for the treatment of deep or systemic mycotic infections made possible by the discovery that when certain fungistatic agents are employed in combination, a synergistic antifungal combination is obtained. The combination not only inhibits the growth of fungi to an extent much greater than that which would result from an additive effect of the components but that such amounts are able to cause irreversible damage to the fungi resulting in a killing or cidal effect on the fungi. The invention also concerns fungicidal compositions which are suitable for use in the treatment of systemic mycotic infections.

DESCRIPTION OF THE INVENTION

The fungicidal composition of the present invention comprises a pyranyl glycine ester compound and a β-lactone compound.

The pyranyl glycine ester compound may be represented by the formula

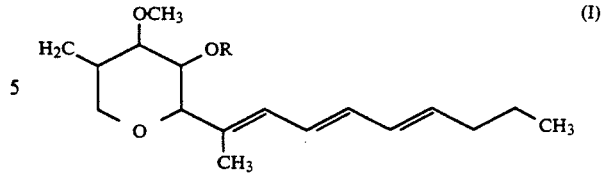

wherein R is —COCH$_2$NH$_2$ or —COCH$_2$N(CH$_3$)$_2$.

The compound in which R is —COCH$_2$NH$_2$ is named (2,3,4,5)-tetrahydro-4-methoxy-5-methyl-2-(1-methyl-1,3,5-nonatrienyl)-2-pyranyl-3-yl-glycine. The compound in which R is —COCH$_2$N(CH$_3$)$_2$ is named (2,3,4,5)-tetrahydro-4-methoxy-5-methyl-2-(1-methyl-1,3,5-nonatrienyl)-2-pyran-3-yl N,N-dimethylglycine.

The compounds may be produced by the fermentation of an unidentified strain of Penicillium isolated from soil and deposited under the Budapest Treaty in the culture collection of the American Type Culture Collection and assigned accession number ATCC 20927. The compound in which R is —COCH$_2$NH$_2$ is the major product in the fermentation and is the preferred compound although mixtures of the two may be advantageously employed. The cultivation, isolation and antifungal properties is the subject of U.S. application, Ser. No. 346,768, filed May, 1989 in the name of O. Hensens et. al., now U.S. Pat. No. 4,952,604 filed Aug. 28, 1990, and the teachings therein are incorporated by reference.

The β-lactone component is selected from compounds which may be defined as (a) a compound having the formula

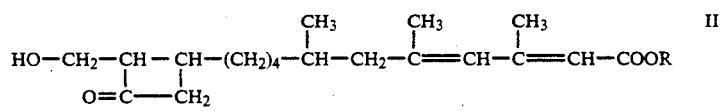

wherein
R is hydrogen or C$_{1-3}$ alkyl; (b) a tetrahydro analog of the compound of formula (II) or (c) a pharmaceutically acceptable salt of (a) or (b).

When R is hydrogen, the compound is named 11-(3-hydroxymethyl-4-oxo-2-oxetanyl)-7-methyl-2,4-undecadienoic acid and may be produced by fungi and is also known as antibiotic 1233A reported by Aldridge et. al., Chem. Comm., 1970, p. 639 and in J. Chem. Soc (c), 1971, pp. 3888-3890 (1972). Other compounds above described and the process for their preparation are disclosed in U.S. Pat. No. 4,751,237, Jun. 14, 1988. The antifungal properties of the compound are disclosed in EPO publication No. 234,752, Sep. 2, 1987.

The pharmaceutically acceptable salts of the β-lactone component include those formed from cations such as sodium, potassium, aluminum, calcium, lithium, magnesium, zinc, and from bases such as ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide.

Of the β-lactone compounds, the preferred compound is 11-(3-hydroxy-methyl-4-oxo-2-oxetanyl)-7-methyl-2,4-undecadienoic acid. A composition comprising the combination of (2,3,4,5)-tetrahydro-4- methoxy-5-methyl-2-(1-methyl-1,3,5-nonatrienyl)-2-pyran-3-yl-glycine (hereinafter "pyranyl glycine ester") and 11-(3-hydroxymethyl-4-oxo-2-oxetanyl)-7-methyl-2,4-undecadienoic acid(hereinafter "β-lactone dienoic acid") as the active components constitutes the preferred embodiment of the present invention.

The synergistic antifungal and fungicidal combinations of the present invention are effective in the treatment of mycotic infections caused by such fungal organisms as Candida species, for example, *C. albicans, C. parapsilosis, C. tropicalis, C. pseudotropicalis, C. krusei, C. rugosa, C. guilliermondii, C. stellatoidea;* those of the Aspergillius species such as *A. fumigatus;* and other disease-causing fungi such as *Cryptococcus neoformans; Torulopsis glabrata; Rhizopus rhizopodiformis; Coccidioides immitis; Sporothrix schenkii; Histoplasma capsulatum;* and *Blastomyces dermatitidis.* Still other fungi against which the combustion may be employed may be represented by *A. niger, C. miyabenmis, F. oxysporium* and *U. zeae.*

The efficacy of the combination of the present invention in producing a synergistic antifungal as well as a fungicidal effect may be seen in the in vitro interaction studies for the determination of activity and determination of viable cells. The effectiveness of the combination may be illustrated with tests against a representative fungal organism known to be the causative agent of mycotic infections, such as *Candida albicans.* Representative synergistic antifungal and fungicidal properties of combinations of the β-lactone compound and pyranyl glycine ester compound are demonstrated against *Candida albicans* as seen in the following examples.

Minimum Inhibitory Concentration of β-Lactone Compound 11-(3-hydroxymethyl-4-oxo-2oxetanyl)-7-methyl-2,4-undecadienoic acid (β-lactone compound), was solubilized in 100 percent dimethylsulfoxide (DMSO). Two-fold dilutions were made with DMSO to obtain final drug concentrations in the broth dilution assay tubes ranging from 0.625 to 10 mg/ml.

The *Candida albicans*, MY 1055 yeast culture, maintained in yeast nitrogen base/glucose (½ percent), YNB/G, was transferred to fresh medium and incubated 7 hours at 37° with shaking at 250 rpm. After incubation, each culture was diluted to $A_{600}=0.0004$ U/ml which was previously determined to be equal to 3000 cfu/ml (colony forming units per milliliter).

1 milliliter of YNB/G inoculated with yeast culture was added to sterile test tubes. The tubes were incubated at 250 rpm, 37° C. for 17 hr. The minimum inhibitory concentration (MIC) was recorded as the lowest concentration of drug showing visible growth.

The minimum inhibitory concentration, against *Candida albicans* MY 1055, was determined to be 3.1 µg/ml.

Minimum Inhibitory Concentration of Pyranyl Glycine Ester Compound

In a similar manner, the pyranyl ester was solubilized in dimethyl sulfoxide and dilution assay tubes from 0.625 to 10 mg/ml prepared. 1 milliliter of YNB/G inoculated with yeast culture was added to assay tubes and incubated at 250 rpm at 37° C. for 17 hrs and minimum inhibitory concentration (MIC) recorded. The MIC against *C. C. albicans* MY 1055 was determined to be 2 µg/ml.

Synergistic and Fungicidal Effect β-Lactone Compound and Pyranyl Glycine Ester Compound Synergistic and fungicidal effects were determined by treating exponential phase *C. albicans* culture with β-Lactone and pyranyl glycine ester at respective MIC level alone and in combination. Exponential phase cultures were prepared by diluting an overnight culture 1:50 or 1:1000 YNB/G. After incubating the diluted cells 7 or 17 hrs. at 37° C., the exponential phase cells were diluted in YNB/G to $A_{600}=0.004$u/ml to obtain 3000 cfu/ml.

10 microliters (µl) of β-lactone compound or pyranyl glycine ester compound prepared in DMSO was added to 1 ml of diluted exponential phase cells. The tubes were incubated at 37° C. at 250 rpm for about 24 hours. Periodically, aliquots were diluted in 0.9% saline and plated on Sabouraud dextrose agar plates to determine the number of cfu/ml.

The results of β-lactone at 3.1 µg/ml and for pyranyl glycine ester at 2 µg/ml along and together are seen in the table and figure.

TABLE I

| | Fungal Growth (CFU/ML) | | | |
|---|---|---|---|---|
| Time (Hours) | No Drug | β-Lactone Compound 3.1 µg/ml | Pyranyl Glycine Ester Compound 2 µg/ml | β-Lactone (3.1 µg/ml) + Pyranyl glycine (2 µg/ml) |
| 0 | $2.70 \times 10^3$ | $2.70 \times 10^3$ | $2.70 \times 10^3$ | $2.70 \times 10^3$ |
| 2 | $4.45 \times 10^3$ | $5.95 \times 10^3$ | $6.05 \times 10^3$ | $2.95 \times 10^3$ |
| 4.5 | $1.75 \times 10^4$ | $4.10 \times 10^3$ | $9.60 \times 10^3$ | $6.95 \times 10^3$ |
| 7.5 | $1.10 \times 10^5$ | $4.55 \times 10^3$ | $1.40 \times 10^4$ | $3.65 \times 10^3$ |
| 16.0 | $5.35 \times 10^6$ | $1.70 \times 10^3$ | $1.00 \times 10^5$ | 5 |
| 20.5 | $5.30 \times 10^7$ | $1.50 \times 10^3$ | $1.02 \times 10^6$ | 1 |
| 24.0 | $7.65 \times 10^7$ | $1.50 \times 10^3$ | $1.37 \times 10^6$ | 1 |

From the foregoing test result and from expected dosage ranges as applied to man, it is determined that generally from about 2.85 to about 4.75 mg/kg of body weight of the pyranyl glycine ester compound and about 2.85 to about 4.75 mg/kg of body weight of the β-lactone compound is to be employed while considering patient's health, weight,a ge and other factors which influence response to a drug as well as the particular drug to be employed. These amounts range of from about 200 to about 400 mg of each active ingredient given BID by oral or parenteral route.

According to the present invention, the synergistic antifungal or fungicidal composition may be formulated for injection and may be present in unit dosage form in ampoules or in multidose containers, if necessary with an added preservative. The compositions may also take such forms as suspensions, solutions or emulsions in oily or aqueous vehicles, and may contain formulating agents such as suspending, stabilizing and/or dispersing agents. Alternatively, the active ingredients may be in powder form for reconstituting with a suitable vehicle prior to parenteral or oral administration.

The compounds also may be prepared in tablet or capsule form as well as in liquid form for oral administration. These also may be in unit dosage form.

For parenteral applications the drugs may be formulated in conventional parenteral solutions such as 0.85 percent sodium chloride or 5 percent dextrose in water, or other pharmaceutically acceptable compositions.

The outstanding properties are most effectively utilized when the pyranyl glycine ester compound and the β-lactone dienoic acid compound are formulated into novel pharmaceutical compositions with a pharmaceutically acceptable carrier according to conventional pharmaceutical compounding techniques.

In preparing the compositions in oral dosage form, the component drugs are intimately admixed with any of the usual pharmaceutical media, including for liguid preparations, liquid carriers such as water, glycols, oils, alcohols, and the like, and for solid preparations such as capsules and tablets, solid carriers such as starches, sugars, kaolin, ethyl cellulose, generally with a lubricant such as calcium stearate, together with binders, disintegrating agents and the like. Because of their ease in administration, tablets and capsules represent the most advantageous oral dosage form. It is especially advantageous to formulate the compositions in unit dosage form for ease of administration and uniformity of dosage. Compositions in unit dosage form constitutes an aspect of the present invention.

The term "unit dosage form" as used in the specification and claims refer to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 200 to 400 milligrams of each of the component drugs.

The following examples illustrate novel compositions useful in the practice of the present invention, but are not to be construed as limiting:

EXAMPLE I 1000 compressed tablets each containing 200 milligrams of pyranyl glycine ester compound and 300 milligrams of β-lactone dienoic acid compound are prepared from the following formulation:

| | Grams |
|---|---|
| Pyranyl glycine ester compound | 200 |
| β-Lactone dienoic acid compound | 300 |
| Starch | 750 |
| Dibasic calcium phosphate hydrous | 5000 |
| Calcium stearate | 2.5 |

The finely powdered ingredients are mixed well and granulated with 10 percent starch paste. The granulation is dried and compressed into tablets.

EXAMPLE II 1000 hard gelatin capsules, each containing 210 milligrams of pyranyl glycine ester compound and 290 milligrams of β-lactone compound are prepared from the following formulation:

| | Grams |
|---|---|
| Pyranyl glycine ester compound | 210 |
| β-Lactone compound | 290 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE III 250 milliliters of an injectable solution are prepared by conventional procedures having the following formulation:

| | Grams |
|---|---|
| Dextrose | 12.5 grams |
| Water | 250 milliliters |
| (2,3,4,5)-tetrahydro-4-methoxy-5-methyl-2-(1-methyl-1,3,5-nonatrienyl)-2-pyran-3-yl-glycine | 150 milligrams |
| 11-(3-hydroxymethyl-4-oxo-2-oxetanyl)-7-methyl-2,4-undecadienoic acid | 250 milligrams |

The ingredients are blended and thereafter sterilized for use.

EXAMPLE IV 1000 hard gelatin capsules, each containing the following may be prepared as in Example II.

| | Grams |
|---|---|
| (2,3,4,5)-Tetrahydro-4-methoxy-5-methyl-2-(1-methyl-1,3,5-nonatrienyl)-2-pyran-3-yl N,N-dimethylglycine | 200 |
| Methyl 11-(3-hydroxymethyl-4-oxo-2-oxetanyl)-7-methyl-2,4-undecadienoate | 300 |
| Starch | 250 |
| Lactose | 750 |
| Talc | 250 |
| Calcium stearate | 10 |

What is claimed is:

1. A method of treating mycotic infections in a patient having such as infection comprising administering to such a patient a fungicidally effective amount of the combination of:
   (1) a pyranyl glycine ester compound which is (2,3,4,5)-tetrahydro-4-methoxy-5-methyl-2-(1-methyl-1,3,5-nonatrienyl)-2-pyranyl-3-yl-glycine; and,
   (2) a-β-lactone compound which is 11-(3-hydroxymethyl-4-oxo-2-oxetanyl)-7-methyl-2,4-undecadienoic acid,
   said pyranyl glycine compound and said β-lactone compound being present at a ratio of β-lactone:-pyranyl glycine of about 3:2 by weight.

2. A method according to claim 1 wherein the treatment is carried out by parenteral administration of said combination.

3. A method according to claim 1 wherein the treatment is by oral administration of said combination.

* * * * *